(12) United States Patent
Wardlaw et al.

(10) Patent No.: US 8,319,954 B2
(45) Date of Patent: *Nov. 27, 2012

(54) VIRTUAL SEPARATION OF BOUND AND FREE LABEL IN A LIGAND ASSAY FOR PERFORMING IMMUNOASSAYS OF BIOLOGICAL FLUIDS, INCLUDING WHOLE BLOOD

(75) Inventors: Stephen C. Wardlaw, Lyme, CT (US); Robert A. Levine, Guilford, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/204,416

(22) Filed: Aug. 5, 2011

(65) Prior Publication Data

US 2011/0294200 A1 Dec. 1, 2011

Related U.S. Application Data

(63) Continuation of application No. 12/417,246, filed on Apr. 2, 2009, now Pat. No. 7,995,194.

(60) Provisional application No. 61/041,784, filed on Apr. 2, 2008, provisional application No. 61/041,791, filed on Apr. 2, 2008, provisional application No. 61/041,790, filed on Apr. 2, 2008, provisional application No. 61/041,794, filed on Apr. 2, 2008, provisional application No. 61/041,797, filed on Apr. 2, 2008, provisional application No. 61/043,571, filed on Apr. 9, 2008.

(51) Int. Cl.
*G01N 33/48* (2006.01)

(52) U.S. Cl. .......... 356/39; 356/244; 356/246; 436/165; 436/164; 436/172; 435/7.1; 435/287.2

(58) Field of Classification Search .................... 356/39, 356/244, 246; 435/287.2, 6, 91.1; 422/69, 422/68.1, 50, 52, 82.05, 82.08; 436/165, 436/154, 172, 63, 66

See application file for complete search history.

(56) References Cited

U.S. PATENT DOCUMENTS

| | | | |
|---|---|---|---|
| 4,023,716 | A | 5/1977 | Shapiro |
| 4,197,088 | A | 4/1980 | Meserol et al. |
| 4,487,081 | A | 12/1984 | DeVaughn et al. |
| 4,615,878 | A | 10/1986 | Kass |
| 5,012,818 | A | 5/1991 | Joishy |
| 5,068,181 | A | 11/1991 | Driscoll |

(Continued)

FOREIGN PATENT DOCUMENTS

DE 10011235 9/2001

(Continued)

OTHER PUBLICATIONS

Fan et al., "Integrated barcode chips for rapid, multiplexed analysis of proteins in microliter quantites of blood," Nature Publishing Group, http://www.nature.com/naturebiotechnology, pp. 1-6, Nov. 2008.

(Continued)

*Primary Examiner* — Layla Lauchman
(74) *Attorney, Agent, or Firm* — O'Shea Getz P.C.

(57) ABSTRACT

Detection and characterization of immunologically detected substances are performed electronically on human and animal biological fluids such as whole blood, serum, plasma, urine, milk, pleural and peritoneal fluids, and semen, which fluids are contained in a thin chamber forming a quiescent fluid sample, which chamber has at least two parallel planar walls, at least one of which is transparent.

27 Claims, 4 Drawing Sheets

U.S. PATENT DOCUMENTS

| | | | |
|---|---|---|---|
| 5,192,511 A | 3/1993 | Roach | |
| 5,284,771 A | 2/1994 | Fan et al. | |
| 5,342,790 A | 8/1994 | Levine et al. | |
| 5,360,719 A | 11/1994 | Levine et al. | |
| 5,447,838 A | 9/1995 | Meiklejohn et al. | |
| 5,454,268 A | 10/1995 | Kim | |
| 5,460,782 A | 10/1995 | Coleman et al. | |
| 5,460,979 A | 10/1995 | Levine et al. | |
| 5,480,778 A | 1/1996 | Levine et al. | |
| 5,593,848 A | 1/1997 | Levine et al. | |
| 5,635,362 A | 6/1997 | Levine et al. | |
| 5,739,042 A | 4/1998 | Frengen | |
| 5,759,794 A | 6/1998 | Levine et al. | |
| 5,768,407 A | 6/1998 | Shen et al. | |
| 5,770,160 A | 6/1998 | Smith et al. | |
| 5,776,710 A | 7/1998 | Levine et al. | |
| 5,834,217 A | 11/1998 | Levine et al. | |
| 6,127,184 A | 10/2000 | Wardlaw | |
| 6,235,536 B1 | 5/2001 | Wardlaw | |
| 6,537,829 B1 | 3/2003 | Zarling et al. | |
| 6,723,290 B1 | 4/2004 | Wardlaw | |
| 6,730,521 B1 | 5/2004 | Cassells | |
| 6,866,823 B2 | 3/2005 | Wardlaw | |
| 6,869,570 B2 | 3/2005 | Wardlaw | |
| 6,929,953 B1 | 8/2005 | Wardlaw | |
| 2002/0028158 A1 | 3/2002 | Wardlaw | |
| 2002/0131902 A1 | 9/2002 | Levy | |
| 2003/0025896 A1 | 2/2003 | Oever et al. | |
| 2003/0224534 A1 | 12/2003 | Kawate | |
| 2004/0048330 A1 | 3/2004 | Bittner | |
| 2004/0165090 A1 | 8/2004 | Ning | |
| 2005/0002826 A1 | 1/2005 | Oguni et al. | |
| 2005/0026197 A1 | 2/2005 | Dertinger | |
| 2005/0277159 A1 | 12/2005 | Lehmann et al. | |
| 2006/0007893 A1 | 1/2006 | Kaplan | |
| 2006/0159962 A1 | 7/2006 | Chandler et al. | |
| 2006/0258018 A1 | 11/2006 | Curl et al. | |
| 2007/0087442 A1 | 4/2007 | Wardlaw | |
| 2007/0243117 A1 | 10/2007 | Wardlaw | |
| 2008/0070317 A1 | 3/2008 | Bradshaw et al. | |

FOREIGN PATENT DOCUMENTS

| | | |
|---|---|---|
| DE | 10240742 | 3/2004 |
| EP | 0366151 | 5/1990 |
| EP | 0642829 | 3/1995 |
| EP | 1239284 | 9/2002 |
| GB | 2254414 | 10/1992 |
| WO | WO 9802727 | 1/1998 |
| WO | WO 0057891 | 5/2000 |
| WO | WO 0223154 | 3/2002 |

OTHER PUBLICATIONS

Sun et al, "Microminiaturized immunoassays using quantum dots as fluorescent label by laser confocal scanning fluorescence detection," Journal of Immunological Methods, Elsevier Science Publishers, vol. 249, No. 1-2, pp. 85-89, Mar. 2001.

Goldman et al., "Multiplexed Toxin Analysis using Four Colors of Quantum Dot Fluororeagents," Analytical Chemistry, American Chemical Society, vol. 76, No. 3, pp. 684-688, Feb. 2004.

Matzdorff et al., "Quantitative assessment of platelets, platelet microparticles, and platelet aggregates in flow cytometry, "The Journal of Laboratory and Clinical Medicine, vol. 131, No. 6, pp. 507-517, Jun. 1998.

Hu Hu et al, "Effects of insulin on platelet and leukocyte activity in whole blood," Thrombosis Research, vol. 107, No. 5, pp. 209-215, Sep. 2002.

Sbrana et al., "Relationships between optical aggregometry (type born) and flow cytometry in evaluating ADP-induced platelet activation," Cytometry, Part B, Clinical Cytometry, vol. 74, No. 1, pp. 30-39, Jan. 2008.

VIRTUAL SEPARATION OF BOUND AND FREE LABEL IN A LIGAND ASSAY FOR PERFORMING IMMUNOASSAYS OF BIOLOGICAL FLUIDS, INCLUDING WHOLE BLOOD

This application is a continuation of U.S. patent application Ser. No. 12/417,246 filed Apr. 2, 2009, which claims the benefit of U.S. Provisional Applications Nos. 61/041,784, filed Apr. 2, 2008; 61/041,791, filed Apr. 2, 2008; 61/041,790, filed Apr. 2, 2008; 61/041,794, filed Apr. 2, 2008; 61/041,797, filed Apr. 2, 2008; and 61/043,571, filed Apr. 9, 2008.

BACKGROUND OF THE INVENTION

1. Technical Field

The present invention relates to the virtual detection, quantization and characterization of immunologically detected substances electronically in human and animal biological fluids such as whole blood, serum, plasma, urine, milk, pleural and peritoneal fluids, and semen, which detection, quantification and characterization is performed in a thin chamber on a quiescent fluid sample, said chamber having at least two parallel planar walls, at least one of which is transparent.

2. Background Information

This invention relates to the improvement in the performance of all immunoassays that presently involve the physical separation of bound from free analyte by, instead, performing a virtual separation of bound and free optically detected label in a ligand assay, wherein the label is preferably a fluorescent label although any optically detectable and quantifiable label will suffice. The chambers for use in this assay and the instruments for measuring the analytes in these chambers are described in the following issued U.S. Pat. Nos. 6,929,953 issued to S. C. Wardlaw; 6,869,570 issued to S. C. Wardlaw; 6,866,823 issued to S. C. Wardlaw; and U.S. Patent Application Publication No. US 2007/0087442, to S. C. Wardlaw, published Apr. 19, 2007.

Physical separation of bound from free analytes have, in the prior art, been accomplished by multiple means including but not limited to, adsorption of the free label by charcoal or talc, magnetic separation of beads containing either the bound or unbound analyte, adsorption of the bound labeled analyte by the container such as antibodies coupled to the wall of a test tube and the use of second precipitation antibodies directed against the analyte binding antibody followed by centrifugation as well as the methods described in the above noted patents and publications.

Some of the types of prior art physical separation of bound target analyte assays are described in the following U.S. Pat. Nos. 5,834,217; 5,776,710; 5,759,794; 5,635,362; 5,593,848; 5,342,790; 5,460,979; 5,480,778; and 5,360,719, all issued to R. A. Levine et al. In the aforementioned patents, the separation of bound from free analyte is performed by centrifugation, or other physical methods, such as decanting, filtration, or the like.

The prior art also describes a type of immunoassay, which is called a "homogeneous immunoassay". Homogeneous immunoassays do not require the physical separation of bound from non-bound, or free, analyte. The "separation of the bound from free" is accomplished by utilizing the steric interference of an enzyme by the relatively large antibody and quantifying the colored or fluorescent products of the enzymatic action. Additional methods of homogeneous assays utilize the fluorescent quenching of fluorophores to distinguish bound from free analyte. While these methods greatly simplify the performance of immunoassays, they are generally useful only for high concentrations of analytes with low molecular weight since the large molecular weight of target analytes such as proteins (e.g., insulin), growth hormones, and the like will also interfere with the enzyme and may affect quenching. Additionally immunoassays of this homogeneous type typically do not have the high sensitivity of standard immunoassays.

It would be highly desirable to provide a ligand assay of a target analyte wherein the quantification of the target analyte is a virtual one which can be performed electronically thereby having the advantages of a homogeneous immunoassay while maintaining the sensitivity of standard immunoassays, as well as the ability to have large size target analytes such as hormones like insulin, growth hormone and the like.

SUMMARY OF THE INVENTION

Immunoassays are used to analyze a wide range of analytes, such as hormones in blood, etc. They work by the general technique of finding a specific binder which specifically binds to the target analyte being measured. A binder is referred to herein as a ligand. Ligands are defined herein as including, but not limited to those antibodies, lectins, aptimers, or naturally occurring substances, that are operative to bind a target analyte. The sample to be measured is admixed with the ligand which is specific to the target analyte, and a labeled version of the analyte to be measured. As this mixture is incubated, the labeled and unlabeled target analyte molecules compete for binding sites on the ligand. After a suitable period, the ligand is removed by any number of ways, and the label bound to the ligand is compared to the label which is unbound and remains free in the mixture. This bound/free ratio relates to the concentration of the target analyte originally in the sample, although either the bound or free label can give the same information. The use of the ratio allows the quality control check wherein the total of bound plus free is relatively constant if the volume is constant. This quality control may also be employed in the practice of this invention.

According to an aspect of the present invention, a method for assaying a biological fluid sample for a target analyte material that may be in the fluid sample is provided. The method utilizes a virtual separation of free and bound target analyte disposed within the fluid sample involving electronic scanning of the sample. The method involves placing the fluid sample in a test chamber having a predetermined and fixed height so as to produce a thin layer of the fluid sample in the chamber. At least one wall of the chamber is transparent, usually the top wall, so that the sample can be observed in the chamber. In certain cases both the top and bottom walls of the chamber are transparent. The height of the chamber (e.g., typically 1µ to 200µ) can vary according to the application at hand. For example, when anticoagulated whole blood is being analyzed, a chamber height of 6µ is advantageous because it creates a monolayer of red blood cells and interspersed plasma lacunae within the blood sample The height of the fixed structure or ligand-coated bead optimally should be no less than one tenth of that of the chamber and ideally approaching the height of the chamber. The reason for this is that if the total amount of label (e.g., fluorophore) present in the free state, surrounding the particle or structure to which the label is bound, is much greater than the amount of the lowest amount of bound label to be detected, the ability to accurately determine the amount of label bound to the bead or structure is diminished due to the influence of signal to noise ratios. Mathematically there is no limit to the height of the chamber but practical limits due to signal to noise of the detected label require a thin chamber and structures occupying at least ten percent of the volume of a cylinder drawn around the periphery of the structure and extending from the base to the tip of the chamber for optimal function. In examples where the ligand is adherent to the chamber top or bottom rather than a structure or bead, the above ratios apply, but the assay optimally should be formulated so that the cylindrical volume above the bound ligand area contains not more than ten times the lowest amount bound to the ligand area that is desired to be detected. This constraint can be diminished by making the chamber as thin as possible or by altering the stoichiometry of the reaction.

The method of this invention can be used to test for drug allergies or allergen sensitivities in patients at the point of care. Drug allergies and allergen sensitivities are a common and important problem. It is expensive to the patient and society. Treating a penicillin allergic patient with a penicillin class drug, for example, can cause death or serious reactions. Penicillin is used in this discussion as a representative drug and because it is the drug type that is the most common cause of severe allergic reactions. The present invention is not limited to testing for penicillin allergies, and can be used to test for sensitivity to other drugs (e.g., antibiotics, muscle relaxants, anesthetics, etc.) and allergens.

Penicillin is an inexpensive, effective and generally non-toxic drug. Patients who think they have a penicillin allergy, can be treated with another less microbial-targeted drug in view of the perceived allergy. Such replacement drugs may cause serious side effects in patients, however, and incur enormous costs to the health care system, since newer medications can be hundreds or thousands of times more expensive then penicillin drugs. Equally importantly are the costs to society associated with the increased development of drug resistant bacteria, viruses, or other infectious agents that occurs when broader spectrum drugs are used instead of drugs more focused on the target organism. It is, therefore, important to individual patients, healthcare providers, and society, to determine the presence or absence of drug allergies or allergen sensitivities by methods in addition to the history given by the patient. One goal of this invention is to detect the presence or absence of drug allergies and/or allegen sensitivities in a sample of a patient's whole blood or plasma.

It is well documented that many patients who claim to be allergic to penicillin are not allergic and similarly some patients who think that they are not allergic may have developed an allergy since their last exposure. There are many reports that about 80% of individuals who believe they are allergic to penicillin will in fact tolerate penicillin use, so for these patients the constraints on antibiotic choice, potentially resulting in less effective, more toxic and more expensive treatment, are unnecessary.

Nowhere is the need for the ability to detect drug allergy more needed than at point of care encounters with the patient. Physicians about to prescribe a medication in their office, the emergency room or hospital do not have the luxury of waiting many hours or a day for the test to be performed either in vitro, or by skin tests. Skin testing may additionally expose the patient to risk of reaction to the testing substance and has the theoretical possibility of inducing allergy or increasing it by an anamnestic response. In vitro tests at present are complex, time consuming to perform and yield information to the physician long after it would be most useful. Additionally the allergenic nature of many drugs, including penicillin type drugs, may be due to more than one epitope and accurate testing would require testing for all common epitopes which may be the cause of the allergic response. RAST testing, well described in the literature, is generally performed on a limited number of test allergens and their epitopes.

It is generally agreed that IgE mediated immune response is the cause of most severe allergic reaction including anaphylaxis, hives, intestinal swelling with diarrhea and respiratory obstruction due to swelling of airways. It is suggested by some experts that other immunoglobulin classes may also contribute to the allergic response to drugs but generally the allergic response to IgG and IgM mediated drug allergies is not life threatening and more likely to be a rash.

An advantage of the present invention is that it provides a means to perform, optimally at the point of care, a determination of the presence of IgE or any other immunoglobulin which has an affinity for one or more drugs that are or may be indicated for use in a given situation.

The label of choice is the use of a fluorophore that is easily detected and attached to the ligand. The present invention is not limited to using fluorometric labels, however. More than one color fluorophore may be used if it is desired to check for the presence or absence of more than one class of immunoglobulin that may become attached to the beads in the same chamber. Beads without the attached antigen are used as controls. The control beads can be chemically and geometrically similar to the coated beads, differing only in color or other means enabling their detection (e.g., fluorescence or combinations of fluorescence dyes incorporated into their structure). The control beads provide a control so that the detection, for example of significant fluorescent signal from the fluorescent labeled antibody directed against the IgE that is attached to the beads containing a determinant (epitope) of the drug being tested as a potential allergen, may be compared to the signal that is present of similar beads not coated or bound to the epitope. Thus, nonspecific binding is controlled and will not result in a false positive.

DETAILED DESCRIPTION OF THE INVENTION

Figure 1:
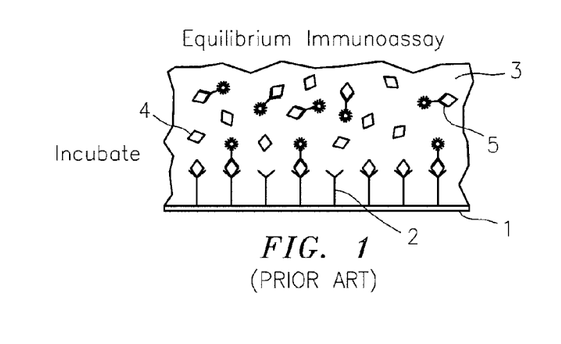
FIG. 1 is a schematic side view of a ligand-bearing surface which may be used to perform an immunoassay on a blood or other sample in accordance with the prior art.
Figure 1A:
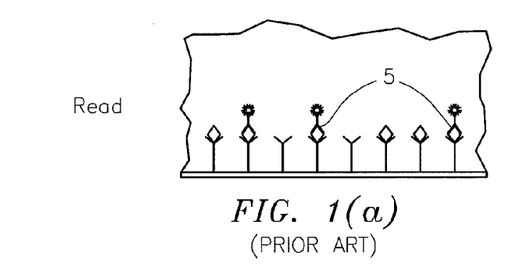
FIG. 1(a) is a view similar to FIG. 1 but showing the surface after the sample has been washed away therefrom in accordance with the prior art.

Referring now to the drawings, FIGS. 1 and 1(*a*) illustrate a prior art competitive immunoassay (also referred to as an "equilibrium assay") which is commonly used for analytes of low molecular weight, such as the thyroid hormone, thyroxin, where the numeral 1 denotes a surface to which a ligand 2, which is specific to the target analyte, is attached by any number of means well-known to the art. Surface 1 may be a transparent wall of a glass or plastic tube or a particle. A solution 3 contains a mixture of the unlabeled target analyte 4 (the unknown) and a labeled target analyte 5. After a period of time, which may be from minutes to hours, depending upon the target and the label, the labeled target analyte 5 and the unlabeled target analyte 4 will be in an equilibrium with each other, wherein many, but generally not all, of the ligand sites 2 will be occupied with either a labeled target analyte 5 or unlabeled target analyte 4. At this point (FIG. 1*a*), the mixture 3 is separated from the ligand-bearing surface 1 in a manner that preserves the labeled target analytes 5 which are bound to the ligand 2. The labeled target analytes 5 bound to the surface 1 are then measured (see FIG. 1*a*), and the free labeled target analytes may also be measured or may be calculated as: Total=Free+Bound, or Bound=Total−Free. The bound to free target analyte ratio is inversely related to the total target analyte amount in the sample.

Figure 2:
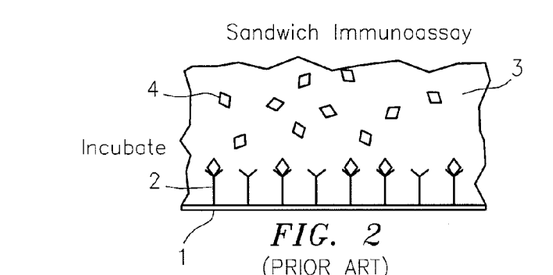
FIG. 2 is a schematic side view similar to FIG. 1, but showing a ligand-bearing surface which may be used to perform a sandwich immunoassay on a blood or other sample in accordance with the prior art.
Figure 2A:
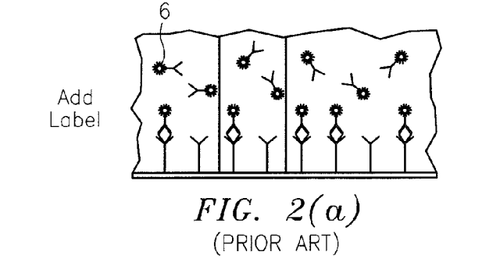
FIG. 2(a) is a view similar to FIG. 2 but showing the sample after a second label has been added to the sample in accordance with the prior art.
Figure 2B:
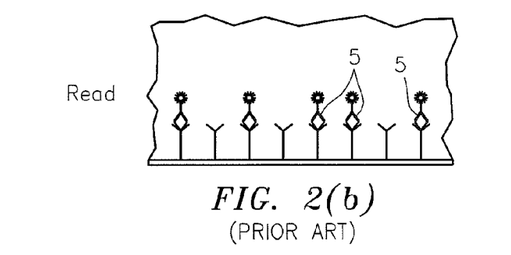
FIG. 2(b) is a view similar to FIG. 2(a) but showing the surface after the sample has been washed away therefrom in accordance with the prior art.

FIG. 2-FIG. 2 (*b*) show a ligand assay often referred to as a "sandwich" assay, where two separate ligands are utilized. Surface 1 has ligand 2 bound ("bound ligand") thereto in a similar manner described above, and the sample containing the target analyte 4 is introduced into the solution 3 and incubated with the surface 1. Either immediately, or after a suitable period of time, a separate labeled ligand 6 is introduced into the solution, which labeled ligand 6 binds to a site on the target analyte 4 which is different than bound ligand 2 (FIG. 2*a*). This, in effect, creates a "sandwich", containing the target analyte 4 in the center. The free labeled ligand 6 is then washed off the surface 1 to leave the surface 1 covered with labeled sites (FIG. 2*b*). The labeled target analytes 4 bound to the surface 1 are then quantified, and the signal therefore is directly proportional to the amount of the target analyte 4 in the original sample. It is generally recognized that the sandwich assay is more precise and somewhat more accurate, but it can only be applied to target analyte molecules which have at least two different sites to which ligands can be bound.

In either of the above assays, the separation of the bound label from the free label is recognized as one of the challenging aspects of the procedure, and often requires one or more mechanically complex steps, such as centrifuging, decanting, washing, etc. As a result, instrumentation to automate these tests has been relatively complex, requiring multiple operations.

Aspects of the present invention, in contrast, provide a means of "virtual separation", wherein the bound and free label are not physically separated, but rather separated by a combination of test cell configuration and mathematical manipulation of the signals from different regions in the test cell. As a result, simplified automated ligand assay methods and apparatus can be performed.

According to aspects of the present invention, immunoassays or ligand assays are performed where the binder is a ligand or other a substance having a high affinity for the target analyte.

Assays according to the present invention can be performed, for example, using the sample containers and imaging instrument systems described in the U.S. Patent Publication Nos. 2007/0243117 and 2007/0087442 and U.S. Pat. No. 6,866,823, all of which are hereby incorporated by reference in their entirety. The present assays are not limited to these chambers and imaging devices, however.

The term "immunoassay" as used in this disclosure and claims shall mean both antibody-based binding agents and non antibody-based binding agents. Examples of the latter include, but are not limited to, intrinsic factors for binding vitamin B12, and avidin for binding biotin-labeled targets or vice versa.

Under aspects of the present invention, a well-defined and physically circumscribed surface is provided to which the ligand is attached, and then the signal from the label bound to that surface is mathematically distinguished from that of any surrounding free label that may reside in solution. There are two general cases which are described as follows.

Figure 3:
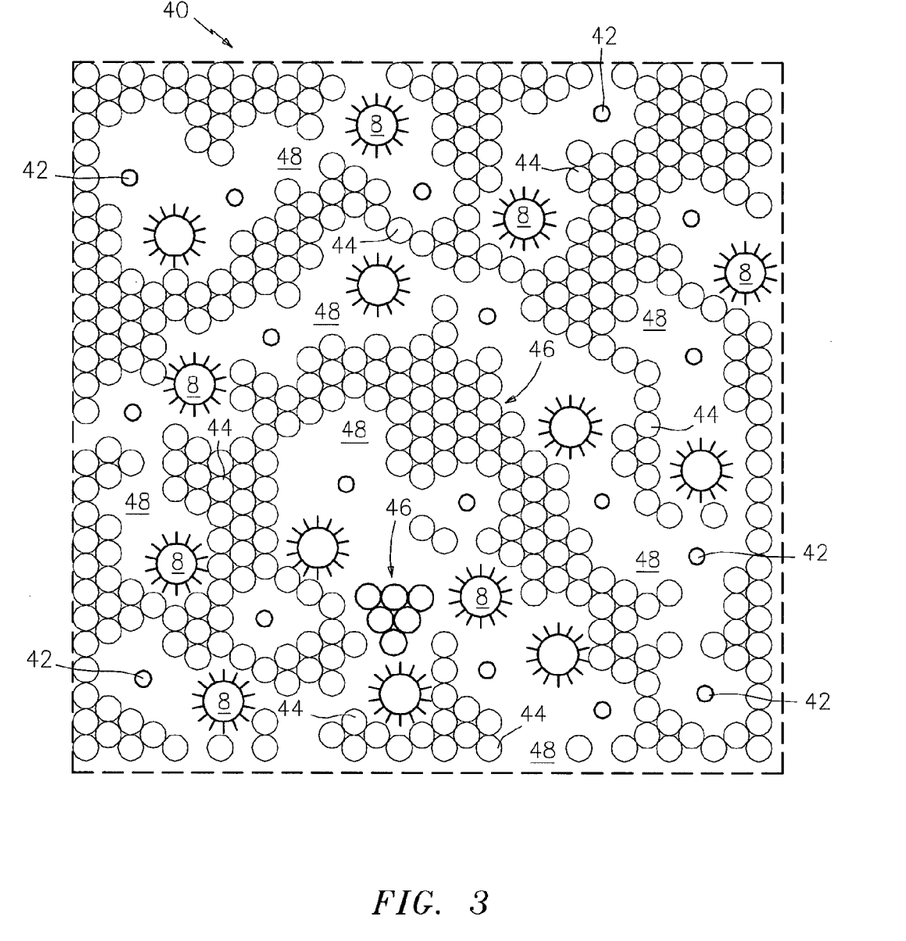
FIG. 3 is a plan view of a first embodiment of a sampling chamber formed in accordance with this invention which contains an anticoagulated whole blood sample to which blood sample ligand-bearing analyte-capturing particles have been added.

FIG. 3 is a plan view of a section of a specimen chamber assembly 40, which chamber assembly 40 contains an anticoagulated whole blood sample. The chamber assembly 40 includes upper and lower walls 7 (see FIG. 4), at least one of which is transparent. Preferably, both of the walls 7 are transparent. The chamber assembly 40 includes spacer members 42 (see FIG. 3) which are randomly located inside of the chamber assembly 40. The spacer members 42 are preferably spherical and determine and control the height of the chamber assembly 40. In the case of assaying an anticoagulated whole blood sample, spacer members 42 having a diameter of about 6μ work particularly well. The blood sample which is contained in the chamber assembly 40 will include individual red blood cells 44 and agglomerations of red blood cells 46. The blood sample also includes clear plasma lacunae areas 48 which do not contain any formed blood components. Finally, the blood sample also includes a plurality of ligand-coated target analyte-capturing particles 8 which are preferably in the form of spheres. The target analyte-capturing particles 8 are randomly distributed throughout the blood sample, and may be about 3μ-4μ in diameter for a blood sample analysis, so that they can be easily detected in the blood sample.

Figure 4:
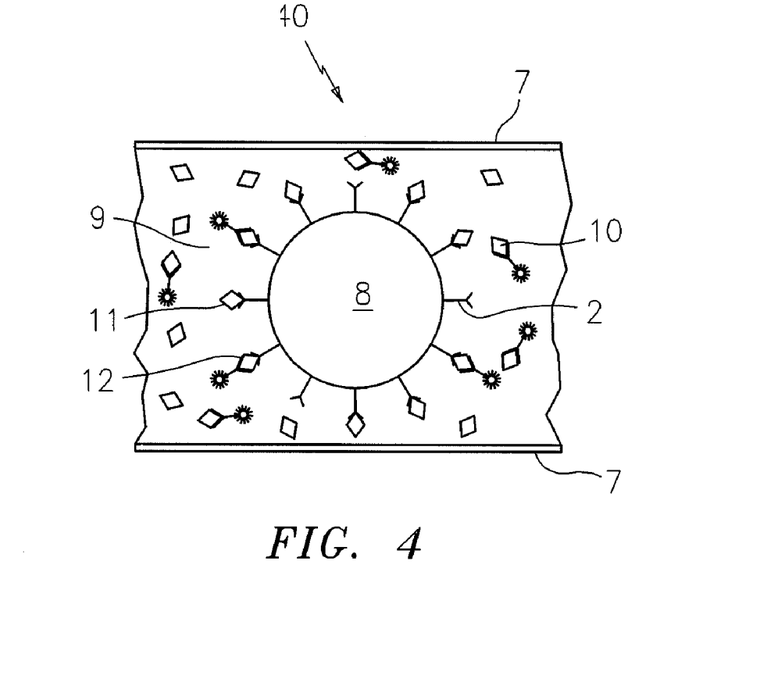
FIG. 4 is a side sectional view of a portion of the sampling chamber of FIG. 3 which contains one of the ligand-coated target analyte-capturing particles.

FIG. 4 shows the structure of the chamber assembly 40 of FIG. 3. The chamber assembly 40 is bounded by top and bottom wall 7, at least one of which must be transparent. Within the chamber is a particle 8, whose surface is covered with a ligand 9. The particle 8 may be any shape as long as its volume can be determined, but it is preferably a sphere. The particle 8 may be of any material to which a ligand can be attached, such as glass, polystyrene, or the like. The particles are not limited to any particular diameter (e.g., 2μ-100μ), and the diameter can vary depending on the fluid being assayed and the height of the chamber being used. The distance between the walls 7 is typically not less than the diameter of the particle 8, but the upper distance limit will depend upon the nature of the particle 8.

A mixture 10 contains both a target analyte 11 and a labeled target analyte 12 in a manner similar to that described in connection with FIG. 1 above. After a suitable period of incubation, the signals from the bound and free target analyte are processed.

Figure 5:
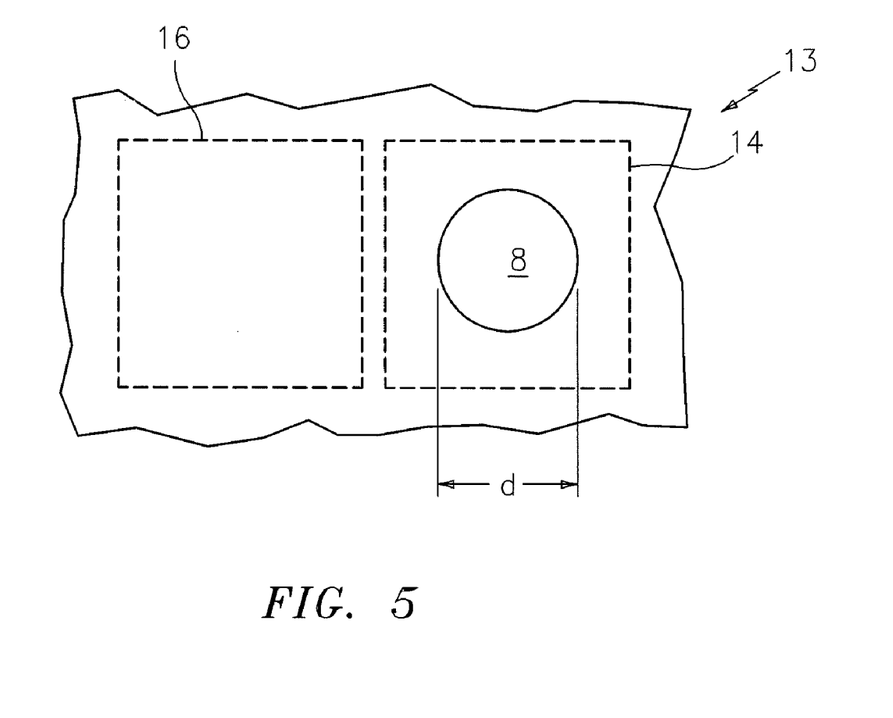
FIG. 5 is a plan view of a test chamber like that shown in FIG. 4, showing an area of the sample containing one of the ligand-coated target analyte-capturing particles and also showing another area of the sample which does not contain one of the ligand-coated target analyte-capturing particles but only contains the free labeled target analyte in the blood sample.

FIG. 5 is a top view of a test chamber assembly like that shown in FIG. 4, showing an undefined expanse 13 of the mixture 10. Within this expanse, the total signal from the label 12 is collected over a defined area 14, which area is not limited to any particular shape. The means of collection can be a fluorescence scanner, in the case of a fluorescent label, or a radio nucleotide scanner, in the case of a radio label. The area is chosen so that it includes at least one particle 8, with a known or measurable diameter. An adjacent defined area 16, not containing a particle, is also measured. The signal from area 16 represents that from the unbound label, since there are no binding sites in that location. The signal from area 14, however, has a signal from both the bound and the free label. The influences of each can be determined in a number of ways. If the particle is spherical, which is a preferred shape, its volume (Vp) can be calculated from its diameter, which can be measured with the same optical system that collects the signal from the label. The volume of the defined areas 14 (V14) and 16 (V16) can be readily calculated from their width and the chamber depth. Assuming that the chamber volumes associated with defined areas 14 and 16 are identical, the signal from the free label is equal to that of the signal from area 16 (S16). This means, that in the absence of signal from the particle (the bound label), the signal from area 14 (Sf) should be: Sf=S16×(V14−Vp). Any signal in excess of this amount is from the bound label (Sb): Sb=S14−Sf. If the volume of the particle is de minimus compared to the volume within the area 14, then the volume correction is not necessary. What is determined is the average label signal intensity per pixel (or collective group of pixels) of the scans. The term pixel as used in this application may include the meaning of one or more adjacent pixels.

Figure 6:
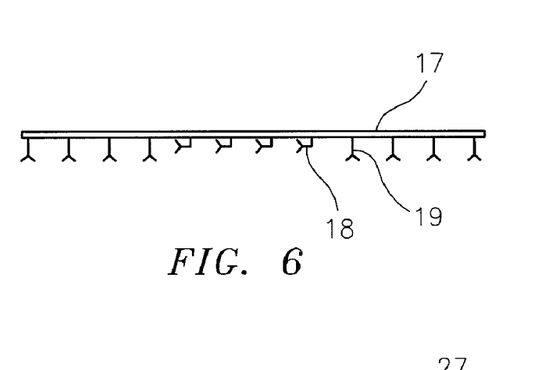
FIG. 6 is a fragmented cross-sectional view of a partially ligand coated target analyte capturing surface wherein portions of the surface are coated with ligands and other portions of the surface are not.

In a second, and most preferred embodiment, ligands are attached to at least one surface of the chamber itself. FIG. 6 shows an (upper) transparent chamber surface 17, which may be glass or plastic, such as acrylic or polystyrene, to which a uniform coating of the ligands has been attached by any number of means well known to the art. After the uniform coating is formed, ligand are selectively removed from one or more regions 18, either by mechanical or chemical means, or by laser ablation, consequently leaving active ligands in adjacent regions 19.

Figure 7:
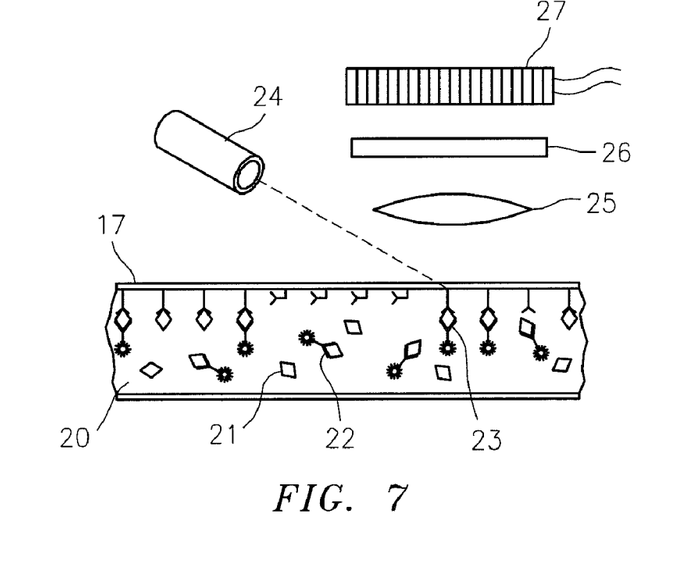
FIG. 7 is a sectional schematic view of a closed chamber having a top surface such as that shown in FIG. 6.

FIG. 7 shows this surface 17 as part of a thin chamber containing mixture 20, comprising unlabeled target analyte 21 and labeled analyte 22. The chamber is preferably less than about 1 mm in height, and is most preferably less than 200μ (e.g., in a range of 1 to 200μ). As before, after a suitable period of time, the labeled and unlabeled analyte will reach equilibrium with the ligand, leaving a portion of the labeled analyte 23 bound to the surface, but only in the region where the ligand remains. In the case of a fluorescent label, the chamber surface 17 is illuminated with light source 24 of the appropriate wavelength to excite fluorescence in the label. Lens 25 collects the fluorescent emissions, which are filtered by optical filter 26 and projected onto an image dissection device 27, which may be a charge couple device (CCD), complimentary metal oxide semiconductor (CMOS), or the like. Alternatively, the light source may be a laser which focuses a tiny, moving spot onto the chamber, and the light collecting device 27 would be, in that case, a simple phototube or photomultiplier.

Figure 8:
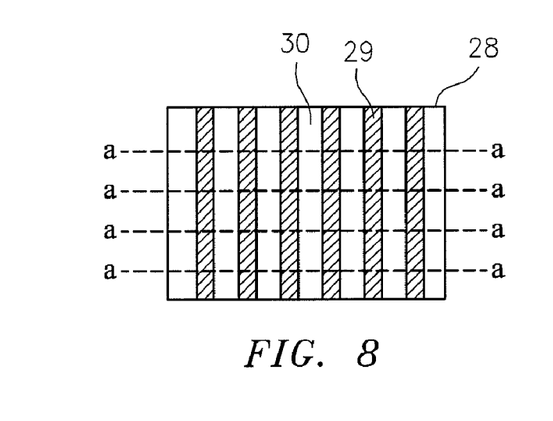
FIG. 8 is a plan view of the surface shown in FIG. 6.
Figure 9:
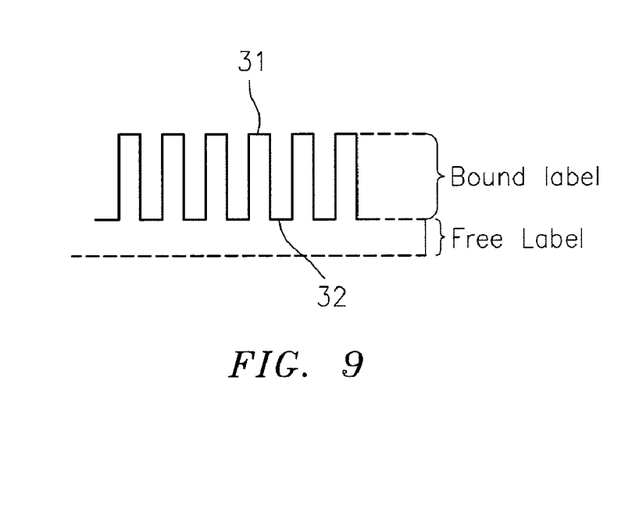
FIG. 9 is a trace of the emissions from the ligand bands on the capture surface shown in FIGS. 6 and 8.

The net result of either process is shown in FIG. 8, which is a schematic top view of the chamber 28, where the active ligand 29 and ablated ligand 30 appear as a series of vertical stripes. The scan lines from the apparatus of FIG. 7 are represented by the lines a-a. FIG. 9 is a representation of the waveform taken across the scan lines a-a, where the peaks 31 are the signal from the active ligand, and the valleys 32 are from the inactive areas. Thus, the bound label concentration is represented by the distance from the peaks to the valleys, and the height of the valleys represents the free label. The active areas and inactive areas are not limited to any particular geometry.

In some embodiments, a chamber wall 17 can be used that is sufficiently flexible that it can be locally elastically deformed by subjecting it to a relatively small point load. The elastic nature of the chamber wall 17 allows a unique option to capture very weak "bound" signals. If the chamber wall 17 is compressed, such as by a small stylus just out of the imaged area, the free label 22 is expelled laterally from the local field of view, and thus its signal is markedly reduced. With this "background" signal reduced, very weak signals from bound label 23 can be detected.

Multiple analytes could be measured simultaneously if the labels fluoresce at different wavelengths, or if the ligand for analyte 1 were at a different physical location in the chamber from the ligand for analyte 2.

An example of a method according to the present invention method includes performing an assay to determine whether a patient may be allergic to one or more drugs (e.g., antibiotics, including penicillin, etc.) or allergens. The assay is performed using a cartridge that has an analysis chamber containing a large number (e.g., thousands) of antibiotic epitope coated beads and uncoated control beads. For those analyses directed toward more than one antibiotic epitope, each particular antibiotic epitope is matched with a particular type of bead for identification purposes. The groups of beads associated with different epitopes can be distinguished from one another using characteristics such as a bead color, size, shape, etc; e.g., epitope A is coated on white beads, epitope B is coated by red beads, etc. A small amount of sample (e.g., 0.5 to 5 micro liters) of capillary or venous anticoagulated whole blood is deposited in the chamber (e.g., drawn into the chamber by capillary action) and upon closing the chamber the blood is directed into an area within the chamber containing the beads. After incubation for a first period of time (e.g., minutes to an hour) immunoglobulin present within the sample binds to those beads coated with a drug (or allergen) to which the immunoglobulin molecule has a specific affinity. Different immunoglobulin molecules present within the sample may have different affinities specific to different drugs (or allergens). The combined beads and blood sample is further mixed with one or more labeled antibodies directed against the immunoglobulin being tested (e.g., Immunoglobulin E ("IgE"), etc.) and allowed to incubate for a second period of time (e.g., seconds to minutes). A fluorophore may be tagged to the antibodies directed against the immunoglobulin being tested to create the "labeled antibody". The sample is then directed into the analysis chamber of the type described above. The actual times needed for incubation for the two steps can be empirically determined and will likely depend upon the avidity and concentration of the antibodies present. The sample disposed within the chamber is analyzed by collecting the signal from the labeled antibodies both free and bound in one or more of the manners described above. If the assay involves the determination of allergy susceptibility of more than one drug, or sensitivity to more than on allergen, the analysis will include distinguishing the bound labeled antibodies as a function of the different types of coated beads as well. The bound label represents those labeled antibodies that are bound to the immunoglobulin being tested, which immunoglobulin is bound to the particle coated with the drug (or allergen) with which the particular immunoglobulin particle has a specific affinity. The amount of label bound on a particle may be calculated by measuring the total signal of the imaged particle and subtracting the surrounding free signal in the immediate area surrounding the particle that is included in the image. Ratios of the amount of label on a given class of coated beads can be calculated by measuring labeled coated and uncoated beads of the same type. Thus, the determination of whether a sample contains immunoglobulin molecules having an affinity for a given drug (or allergen) can be performed by practicing the present invention. In addition, simultaneous detection of an allergy to more than one drug (or sensitivity to more than one allergen) can be performed under the present invention using different types of detectable beads or particles, with each type coated with a different drug (or allergen). A single type particle (or bead) may be used as a control particle for all the drug allergy (allergen sensitivity) tests if the particle is the same in size and composition as the coated particles. If necessary, more than one type of control particle may be used with the size of the control particle matching the size of the drug or allergen coated particles to which it is being compared.

In some embodiments, after the second incubation (the one containing the labeled ligand) the method includes the step of adding a liquid containing no label to the sample containing unbound label disposed within the chamber, thereby leaving primarily the label attached to the immobilized beads or structures. The virtual separation of bound from free is subsequently performed as previously stated but the removal of the liquid containing the label can serve to increase sensitivity of the assay at the expense of complexity. Since the total capacity of the chamber and the amount of liquid in the chamber is in the range of less than one to several micro liters, the addition of a label-free fluid to the chamber in a substantial volume (e.g., tens of micro liters) will remove much of the fluid containing label and the remaining free label signal will be removed by the utilization of the virtual separation of bound from free process.

The above described methodology provides a novel and desirable technique for determining the amount of bound and free labeled target analyte within areas of a chamber that contain ligands or are free of ligands specific to that target analyte within a sample, and thereby provides qualitative and quantitative information relative to the sample. In some instances, qualitative information such as knowing whether the target analyte is present or absent in the sample is sufficient information for the analysis at hand. An example of such an instance is the determination of whether a specimen has specific IgE directed against a given drug, when the absence of such IgE is the normal state. If more quantitative information is desired (e.g., the concentration of the target analyte in the sample), the obtained bound/free information may be used with a standard curve, which curve is empirically derived for the particular target analyte and sample being considered, to determine the quantitative information; e.g., the amount of target analyte within the sample. Standard curves operable to be used with all types of immunoassays are known and the present invention is not limited to any particular standard curve. Sample curves may be performed prior to or concurrently with the assay and the results stored on the instrument performing the analysis.

Although the invention has been shown and described with respect to specific detailed embodiments thereof, it will be understood by those skilled in the art that various changes in form and detail thereof may be made without departing from the spirit and the scope of the invention.

What is claimed is:

1. An apparatus for performing a target analyte immunoassay of a fluid sample including a detectable label, which label is operative to bind to the target analyte to produce labeled target analyte, which labeled target analyte is detectable in the sample, the apparatus comprising:
a sample chamber having at least one first surface area that has target analyte specific ligands attached to it, which target analyte-specific ligands are operative to selectively bind target analyte present in the sample to the first surface area, the sample chamber having at least one second surface area that is free of target analyte-specific ligands operative to selectively bind target analyte present in the sample to the second surface area; and
an imaging device adapted to optically scan the at least one first area to detect and record an average label signal intensity per pixel distribution of the labeled target analyte in the at least one first area, and adapted to optically scan the at least one second area to detect and record an average label signal intensity per pixel distribution of the labeled target analyte in the at least one second area, and adapted to determine at least one of an amount of labeled target analyte in the at least one first area, an amount of labeled target analyte in the at least one second area, and a ratio of labeled target.

2. The apparatus of claim 1 wherein the chamber has a height of 1 to 200μ.

3. The apparatus of claim 2 wherein the chamber has a height of about 6μ.

4. The apparatus of claim 1 wherein the chamber has a height in the range of 3μ to 15μ.

5. The apparatus of claim 1, wherein the chamber has at least one wall, and the at least one first surface area and the at least one second surface area are disposed on the wall.

6. The apparatus of claim 1, wherein the chamber includes one or more objects disposed within the chamber, wherein at least one of the at least one first surface area and the at least one second surface area is disposed on one of the objects disposed within the chamber.

7. The apparatus of claim 1, wherein the imaging device is further adapted to determine a total amount of the target analyte in the fluid sample using a determined total amount of labeled target analyte within the first surface areas of the chamber and a determined total amount of labeled target analyte in the second areas of the chamber.

8. The apparatus of claim 7, wherein the imaging device is further adapted to determine a total amount of bound target analyte in the fluid sample using the determined total amount of labeled target analyte in the fluid sample, and the determined total amount of labeled target analyte in the second areas of the chamber.

9. The apparatus of claim 1, wherein the detectable label is a detectable fluorescent molecule.

10. An apparatus for performing a target analyte immunoassay of a fluid sample including a detectable label attached to a first ligand, which first ligand is specific to an epitope of the target analyte, which first ligand is operative to bind to the target analyte to produce labeled ligand target analyte, which labeled ligand target analyte is detectable in the sample, the apparatus comprising:
a sample chamber having at least one first surface area having target analyte specific second ligands attached to it, which target analyte-specific second ligands are operative to selectively bind target analyte present in the sample to the first surface area, and at least one second surface area that is free of target analyte-specific second ligands operative to selectively bind target analyte present in the sample to the second surface area;
an imaging device adapted to optically scan the at least one first area to detect and record an average label signal intensity per pixel distribution of the labeled ligand target analyte in the at least one first area, and adapted to optically scan the at least one second area to detect and record an average label signal intensity per pixel distribution of the labeled ligand target analyte in the at least one second area, and adapted to determine at least one of an amount of labeled ligand target analyte in the at least one first area, an amount of labeled ligand target analyte in the at least one second area, and a ratio of labeled ligand target analyte in the first and second areas.

11. The apparatus of claim 10, wherein the target analyte is an immunoglobulin of a given sub type.

12. The apparatus of claim 10, wherein the sample chamber includes first particles, and the first surface areas are disposed on the first particles.

13. The apparatus of claim 12, wherein the first particles are a first type of particle coated with a first drug.

14. The apparatus of claim 12, wherein the sample chamber includes second particles, and the second surface areas are disposed on the second particles, which second particles are of the first type and free of a drug coating.

15. The apparatus of claim 10, wherein the sample chamber includes first particles of a first type and second particles of a second type, and the first surface areas are disposed on the first particles, and the second type is different from the first type.

16. The apparatus of claim 15, wherein the first particles are coated with a first drug, and the second particles are coated with a second drug, which second drug is different from the first drug.

17. The apparatus of claim 15, wherein the second surface areas are disposed on third particles, which third particles are of the first or second type and free of a drug coating.

18. The apparatus of claim 10, wherein the sample chamber has a height in the range of 3µ to 15µ.

19. A sample chamber for performing a target analyte immunoassay of a fluid sample that includes a detectable label, which label is operative to bind to the target analyte to produce labeled target analyte, which labeled target analyte is detectable in the sample, the sample chamber comprising:

at least one first surface area, which first surface area has target analyte specific ligands attached to it, which target analyte-specific ligands are operative to selectively bind target analyte present in the sample to the first surface area; and at least one second surface area in the chamber which is free of target analyte-specific ligands operative to selectively bind target analyte present in the sample to the second surface area.

20. The sample chamber of claim 19, wherein the chamber has at least one wall, and the at least one first surface area and the at least one second surface area are disposed on the wall.

21. The sample chamber of claim 19, wherein the chamber includes at least one object disposed within the chamber, wherein at least one of the at least one first surface area and the at least one second surface area is disposed on one of the objects disposed within the chamber.

22. The sample chamber of claim 19, further comprising first particles, and the first surface areas are disposed on the first particles.

23. The sample chamber of claim 22, wherein the first particles are a first type of particle coated with a first drug.

24. The sample chamber of claim 23, further comprising second particles, and the second surface areas are disposed on the second particles, which second particles are of the first type and free of a drug coating.

25. The sample chamber of claim 19, further comprising first particles of a first type and second particles of a second type, and the first surface areas are disposed on the first particles, and the second type is different from the first type.

26. The sample chamber of claim 25, wherein the first particles are coated with a first drug, and the second particles are coated with a second drug, which second drug is different from the first drug.

27. The sample chamber of claim 25, wherein the second surface areas are disposed on third particles, which third particles are of the first or second type and free of a drug coating.

* * * * *